(12) United States Patent
Sell (10) Patent No.: US 10,588,601 B2
(45) Date of Patent: Mar. 17, 2020

(54) ULTRASOUND PROBE SANITIZATION INDICATOR AND STORAGE SYSTEM AND METHOD OF USE

(71) Applicant: Dale Sell, Bushland, TX (US)

(72) Inventor: Dale Sell, Bushland, TX (US)

( * ) Notice: Subject to any disclaimer, the term of this patent is extended or adjusted under 35 U.S.C. 154(b) by 335 days.

(21) Appl. No.: 15/346,997

(22) Filed: Nov. 9, 2016

(65) Prior Publication Data

US 2018/0125452 A1 May 10, 2018

(51) Int. Cl.
*A61B 8/00* (2006.01)
*B65D 85/00* (2006.01)

(52) U.S. Cl.
CPC .......... *A61B 8/4422* (2013.01); *A61B 8/4433* (2013.01); *A61B 8/4438* (2013.01); *B65D 85/70* (2013.01)

(58) Field of Classification Search
CPC ... A61B 1/00; A61B 1/00137; A61B 1/00144; A61B 8/00; A61B 8/44; A61B 8/4422; A61B 8/4433; A61B 8/4438; A61B 19/00; A61B 19/02; A61B 19/0256; A61B 19/026; A61B 19/0264; A61L 2/26; A61L 2/28; B65B 55/00; B65B 55/10; B65D 85/00; B65D 85/70
USPC .......................................... 206/363–370, 438
See application file for complete search history.

(56) References Cited

U.S. PATENT DOCUMENTS

| | | | |
|---|---|---|---|
| 2,830,003 A | 4/1958 | Mason et al. | |
| 4,212,153 A | 7/1980 | Kydonieus et al. | |
| 5,699,326 A | 12/1997 | Haas et al. | |
| D394,675 S | 5/1998 | Haas et al. | |
| 6,086,971 A | 7/2000 | Haas et al. | |
| 6,197,396 B1 | 3/2001 | Haas et al. | |
| 7,215,604 B2 | 5/2007 | Haas et al. | |
| 7,870,959 B2* | 1/2011 | Kuo | A61L 2/26 206/363 |
| 8,333,750 B2 | 12/2012 | Tanaka et al. | |
| 9,277,966 B2* | 3/2016 | Seitz, III | A61M 25/002 |
| 2005/0116014 A1* | 6/2005 | Vogt | B65D 27/005 229/68.1 |
| 2009/0123332 A1* | 5/2009 | Whitehead | B65D 33/004 206/459.1 |
| 2012/0010468 A1* | 1/2012 | Afridi | A61B 1/00059 600/121 |
| 2015/0068939 A1* | 3/2015 | Seitz, III | A61M 25/002 206/363 |

(Continued)

FOREIGN PATENT DOCUMENTS

WO WO2000071433 A1 11/2000

*Primary Examiner* — Bryon P Gehman
(74) *Attorney, Agent, or Firm* — Shannon Warren (57) ABSTRACT

A probe sleeve for holding a probe in various stages of cleanliness with indicators thereto. The probe sleeve comprising an envelope portion, a sealing system, and a plurality of indicator zones. The envelope portion comprising a mouth. The mouth is operative to receive and release the probe. The envelope is operative to hold the probe. The plurality of indicator zones comprise a first indicator zone and a second indicator zone. The plurality of indicator zones display a status indicator related to the state of the probe. The sealing system is configured to selectively close and open the mouth. The first indicator zone is operable to signify that the probe is clean. The second indicator zone is operable to signify that the probe is not clean.

11 Claims, 11 Drawing Sheets

(56) References Cited

U.S. PATENT DOCUMENTS

| | | | |
|---|---|---|---|
| 2015/0069728 A1* | 3/2015 | Seitz, III | A61B 1/0014 |
| | | | 206/305 |
| 2015/0090620 A1* | 4/2015 | Seitz, III | A61M 25/002 |
| | | | 206/363 |
| 2016/0058270 A1* | 3/2016 | Seitz, III | A61M 25/002 |
| | | | 206/363 |

* cited by examiner

ULTRASOUND PROBE SANITIZATION INDICATOR AND STORAGE SYSTEM AND METHOD OF USE

CROSS-REFERENCE TO RELATED APPLICATIONS

Not applicable.

STATEMENT REGARDING FEDERALLY SPONSORED RESEARCH OR DEVELOPMENT (IF APPLICABLE)

Not applicable.

REFERENCE TO SEQUENCE LISTING, A TABLE, OR A COMPUTER PROGRAM LISTING COMPACT DISC APPENDIX (IF APPLICABLE)

Not applicable.

BACKGROUND OF THE INVENTION

This disclosure relates generally to an ultrasound probe sanitization indicator and storage system and method of use. Examples of similar disclosures can be found at U.S. Pat. Nos. 4,212,153, 5,699,326, 7,215,604, D394,675, 6,197,396, 6,086,971, 8,333,750 B2 and WO2000071433 A1. However, none of the known inventions and patents, taken either singularly or in combination, is seen to describe the instant disclosure as claimed. Accordingly, an ultrasound probe sanitization indicator and storage system and method of use would be advantageous.

BRIEF SUMMARY OF THE INVENTION

A probe sleeve for holding a probe in various stages of cleanliness with indicators thereto. The probe sleeve comprising an envelope portion, a sealing system, and a plurality of indicator zones. The envelope portion comprising a mouth. The mouth is operative to receive and release the probe. The envelope is operative to hold the probe. The plurality of indicator zones comprise a first indicator zone and a second indicator zone. The plurality of indicator zones display a status indicator related to the state of the probe. The sealing system is configured to selectively close and open the mouth. The first indicator zone is operable to signify that the probe is clean. The second indicator zone is operable to signify that the probe is not clean. The sealing system comprises a flap portion. The flap portion comprises a one or more adhesive strips. The one or more adhesive strips are operable to selectively close a portion of the flap portion over the mouth. The one or more adhesive strips comprise a first strip and a second strip. The flap portion comprises a first flap portion and a second flap portion. The first flap portion comprises the first strip. The second flap portion comprises the second strip. The flap portion comprises a perforation between the first flap portion and the second flap portion. The first indicator zone is arranged on top of the first indicator zone. The first indicator zone comprises a first side and a second side. The second side comprises an adhesive. Removing the first indicator zone from the second indicator zone exposes a portion of the second indicator zone. The first flap portion with the first strip are configured to attach to a portion of the first indicator zone. The first indicator zone is configured to remove the first flap portion with the first strip when opening the probe sleeve to remove the probe.

A probe sleeve for holding a probe in various stages of cleanliness with indicators thereto. The probe sleeve comprising an envelope portion, a sealing system, and a plurality of indicator zones. The envelope portion comprising a mouth. The mouth is operative to receive and release the probe. The envelope is operative to hold the probe. The plurality of indicator zones comprise a first indicator zone and a second indicator zone. The plurality of indicator zones display a status indicator related to the state of the probe. The sealing system is configured to selectively close and open the mouth. The first indicator zone is operable to signify that the probe is clean. The second indicator zone is operable to signify that the probe is not clean.

A method of using a probe sleeve, comprising: cleaning a probe, inserting the probe into a probe sleeve, indicating a date marking on a label on the probe sleeve related to a date of cleaning the probe, sealing a portion of the probe within the probe sleeve with a sealing system, and removing the probe from the probe sleeve and removing a first indicator zone so as to signify that the probe is no longer clean. The probe sleeve comprises an envelope portion, the sealing system, and a plurality of indicator zones. The envelope portion comprising a mouth. The mouth is operative to receive and release the probe. The envelope is operative to hold the probe. The plurality of indicator zones comprise the first indicator zone and a second indicator zone. The plurality of indicator zones display a status indicator related to the state of the probe. The sealing system is configured to selectively close and open the mouth. The first indicator zone is operable to signify that the probe is clean. The second indicator zone is operable to signify that the probe is not clean.

DETAILED DESCRIPTION OF THE INVENTION

Described herein is an ultrasound probe sanitization indicator and storage system and method of use. The following description is presented to enable any person skilled in the art to make and use the invention as claimed and is provided in the context of the particular examples discussed below, variations of which will be readily apparent to those skilled in the art. In the interest of clarity, not all features of an actual implementation are described in this specification. It will be appreciated that in the development of any such actual implementation (as in any development project), design decisions must be made to achieve the designers' specific goals (e.g., compliance with system- and business-related constraints), and that these goals will vary from one implementation to another. It will also be appreciated that such development effort might be complex and time-consuming, but would nevertheless be a routine undertaking for those of ordinary skill in the field of the appropriate art having the benefit of this disclosure. Accordingly, the claims appended hereto are not intended to be limited by the disclosed embodiments, but are to be accorded their widest scope consistent with the principles and features disclosed herein.

Figure 1:
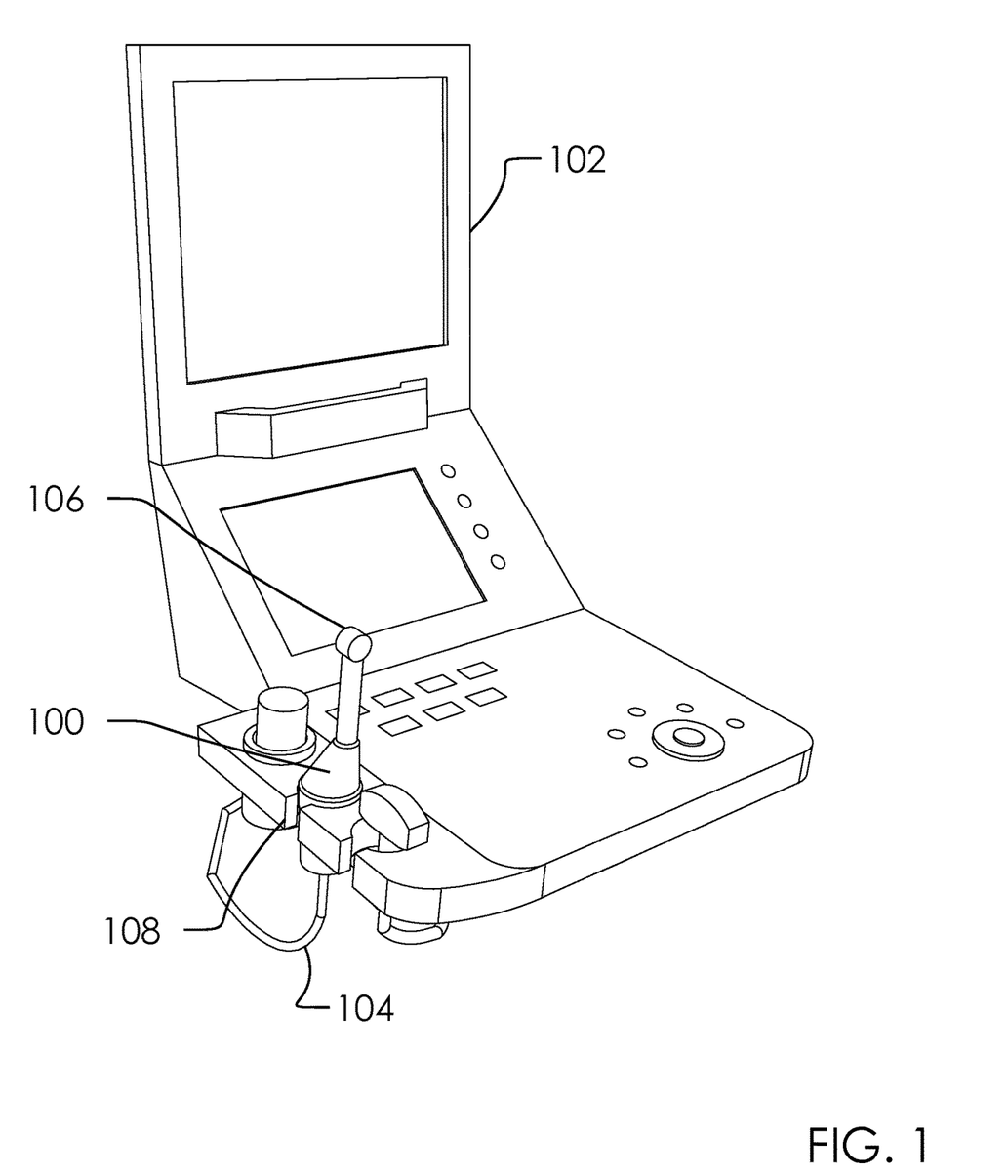
FIG. 1 illustrates a probe 100 attached to a scanning machine 102.

FIG. 1 illustrates a probe 100 attached to a scanning machine 102.

In one embodiment, said probe 100 with said scanning machine 102 can be used for various medical procedures, such as a medical ultrasonography test; diagnostic sonography such as imaging internal body structures including vessels, tendons, muscles, joints and internal organs. As is known in the art, said probe 100 can be sued for examining pregnant women in a procedure known as obstetric sonography. In one embodiment, said scanning machine 102 can comprise a cradle 108 affixed to a portion of said scanning machine 102. In one embodiment, said scanning machine 102 selectively holds said probe 100 in said cradle 108. In one embodiment, said probe 100 can comprise a probe sensor 106 which can be inserted into a portion of a patient.

As a practical matter, however, since technicians are often in a hurry, they are unable to care for said probe 100 in a sanitary manner. It is not uncommon for said probe 100 to be sat down on said probe 100 without regard for the sanitation. Likewise, as noted below in FIG. 5, other storage locations give no indication as to the sanitization status of said probe 100.

In one embodiment, said probe sensor 106 and other portions of said probe 100 can be covered by an endovaginal ultrasound probe covers before use, which has come to be known as being "dressed" for use.

Unfortunately, when said probe 100 is stored in said cradle 108 of said probe 100, it is unclear whether said probe 100 is actually sanitized.

Figure 2:
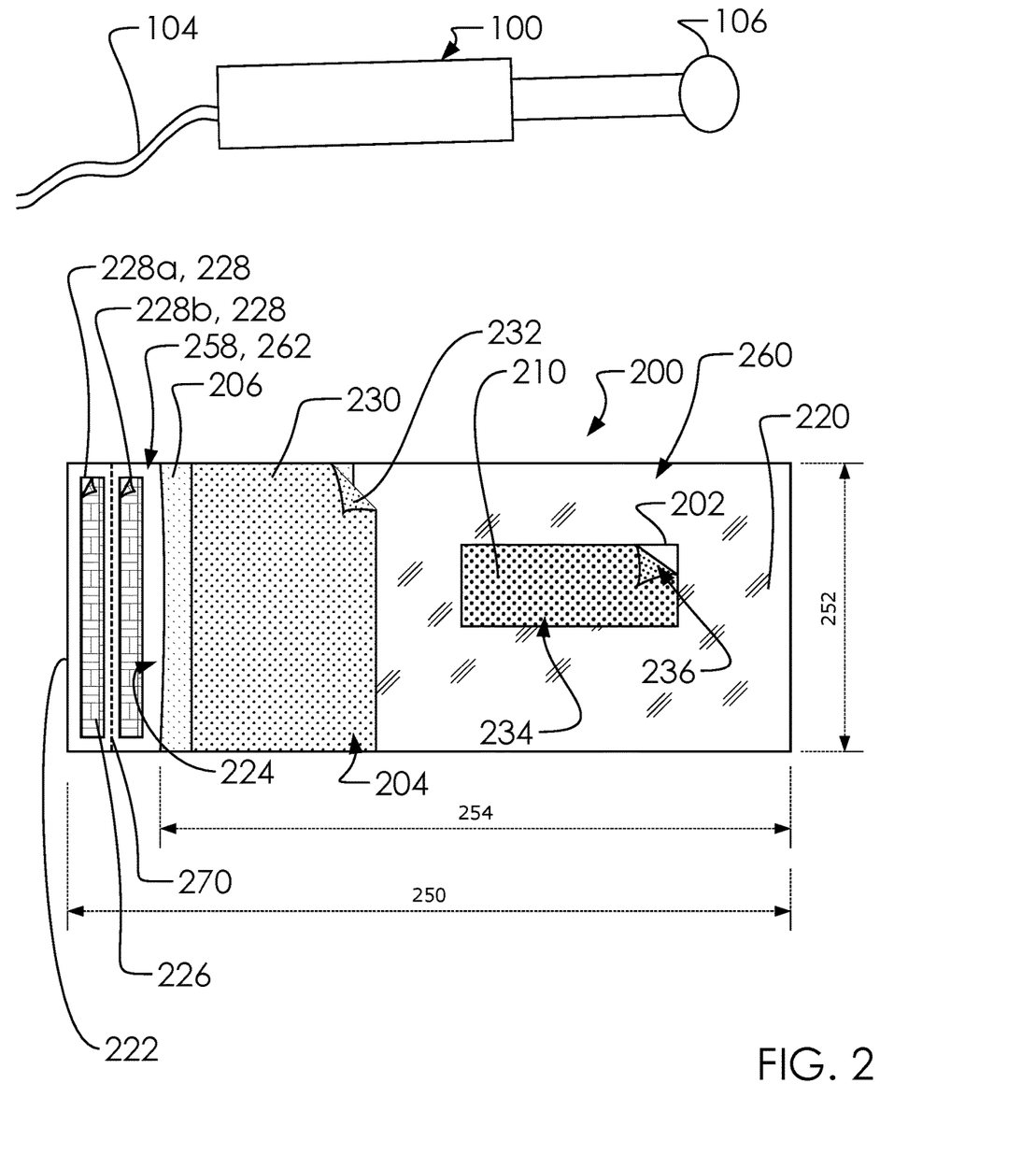
FIG. 2 illustrates an elevated overview of a probe sleeve 200 and said probe 100.

FIG. 2 illustrates an elevated overview of a probe sleeve 200 and said probe 100.

In one embodiment, said probe sleeve 200 can comprise a label 202, a first indicator zone 204, a second indicator zone 206, a label cover 210, a first end 220, a second end 222, a one or more adhesive strips 228 having a one or more adhesive covers 226, a length 250, a height 252, an envelope width 254, a sealing system 258, and an envelope portion 260. In the case of said probe sleeve 200, said sealing system 258 can comprise a flap portion 262. In one embodiment, said sealing system 258 can selectively close over said mouth 224.

In one embodiment, a portion of said probe 100 can be stored in said envelope portion 260 of said probe sleeve 200. In one embodiment, said flap portion 262 can enclose around a portion of said probe 100.

In one embodiment, said first indicator zone 204 can comprise a first color, such as green. Said second indicator zone 206 can comprise a second color, such as red. In one embodiment, said first indicator zone 204 and said second indicator zone 206 can be arranged so as to overlap; wherein, with said first indicator zone 204 attached to said probe sleeve 200, said second indicator zone 206 is substantially covered and not visible. In one embodiment, with said first indicator zone 204 removed, said second indicator zone 206 can be seen whether or not said flap portion 262 is closed over said mouth 224 of said envelope portion 260. More discussion of these features can be found infra.

In one embodiment, said one or more adhesive strips 228 can be of the type known in the art for sealing envelopes. The presence of a plurality of strips may be required to move said probe sleeve 200 through a variety of stages, as discussed below. In one embodiment, said one or more adhesive strips 228 can comprise a first strip 228a and a second strip 228b.

In one embodiment, said first indicator zone 204 can comprise a first side 230 and a second side 232. In one embodiment, said first side 230 can comprise said green color and said second side 232 can comprise an adhesive for releaseably attaching said first indicator zone 204 to said second indicator zone 206. In one embodiment, a portion of said second indicator zone 206 can be releaseably covered by said first indicator zone 204.

In one embodiment, said length 250 can comprise 15 inches, said height 252 can comprise 3-5 inches. In one embodiment, said envelope portion 260 can comprise said envelope width 254.

In one embodiment, said label 202 can received text such as information about the last date sanitized. Said label 202 can be releaseably covered by a label cover 210. In one embodiment, said label cover 210 can comprise a first side 234 and a second side 236. In one embodiment, said second side 236 can comprise an adhesive and said first side 234. In another embodiment, said label cover 210 can be substantially opaque. In one embodiment, with said label cover 210 affixed to said label 202, a user of said probe sleeve 200 is to understand that the envelope has not be used as of yet.

In one embodiment, a portion of said first indicator zone 204 can be removed to display substantially all of said second indicator zone 206.

In one embodiment, said one or more adhesive covers 226 can comprise a perforation 270 between said one or more adhesive strips 228.

Figure 3:
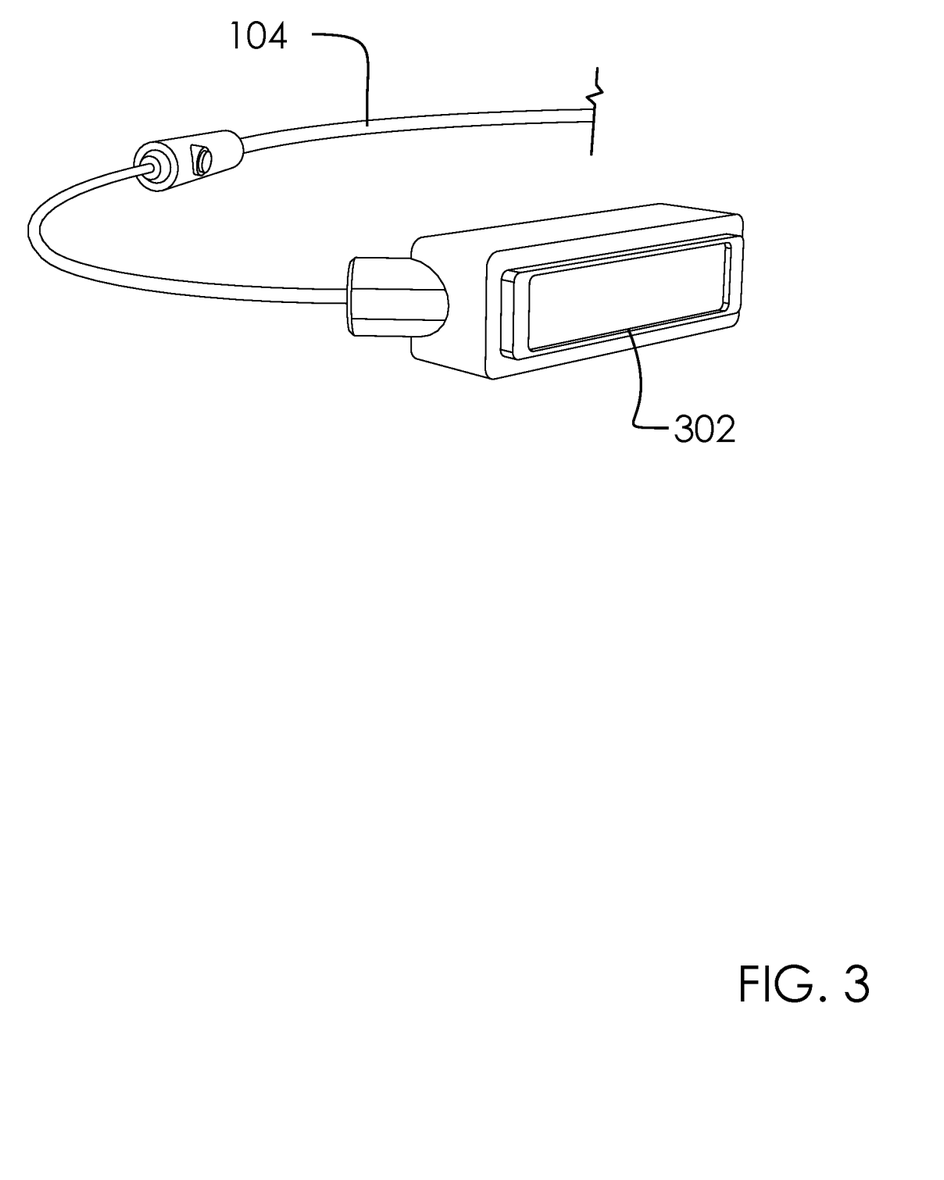
FIG. 3 illustrates a perspective overview of a plug 302 and a portion of said probe cord 104.

FIG. 3 illustrates a perspective overview of a plug 302 and a portion of said probe cord 104.

As is known in the art, said plug 302 can plug into said scanning machine 102 and said probe cord 104 can carry a signal between said scanning machine 102 and said probe 100.

Figure 4:
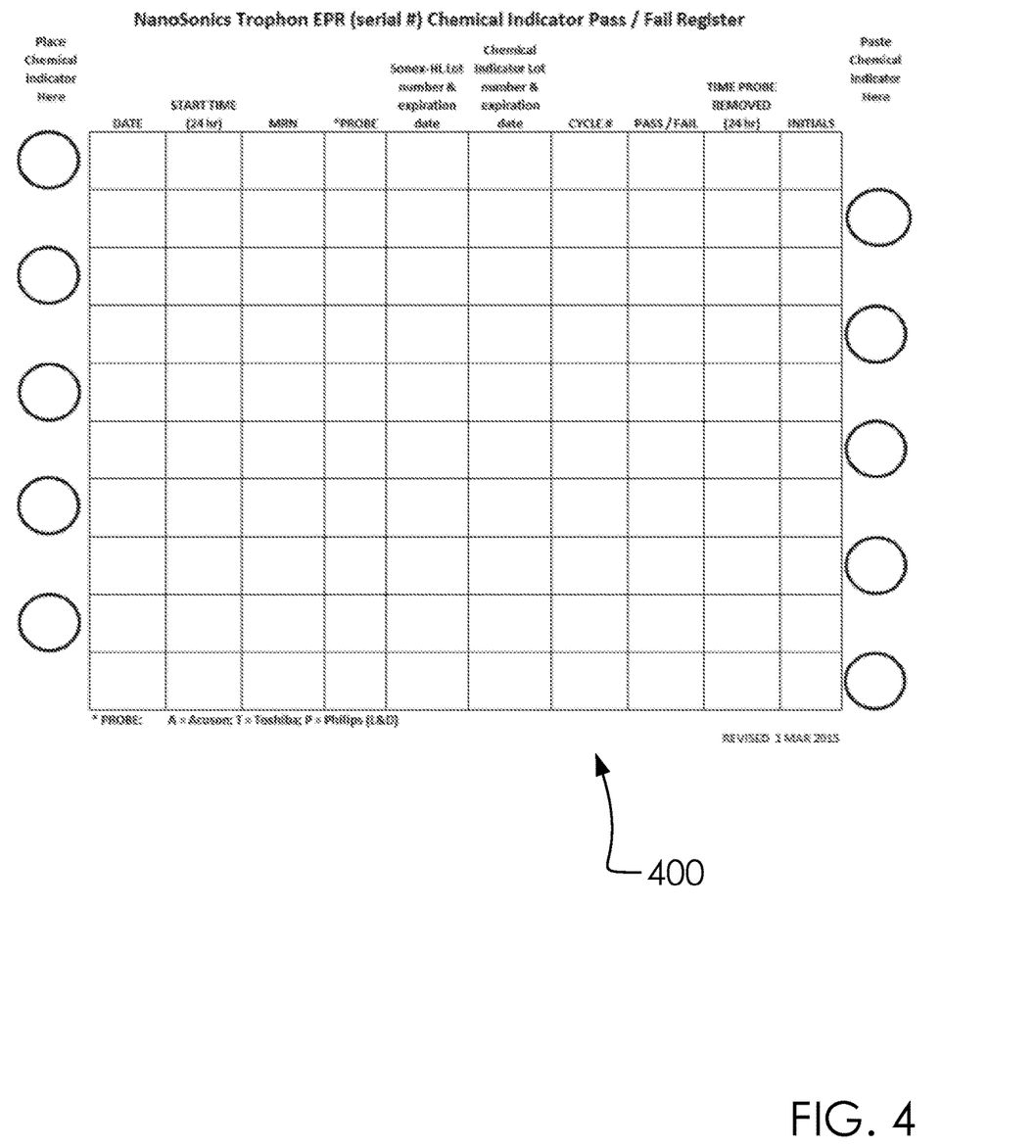
FIG. 4 illustrates a cleaning log 400.

FIG. 4 illustrates a cleaning log 400.

In one embodiment, said probe 100 can be cleaned and a record of that cleaning can be kept on a record of that cleaning on said cleaning log 400. Of course, this approach is only as good as staff time and diligence allows. Where a staff member forgets to log on this sheet, the results can be unfortunate.

Figure 5:
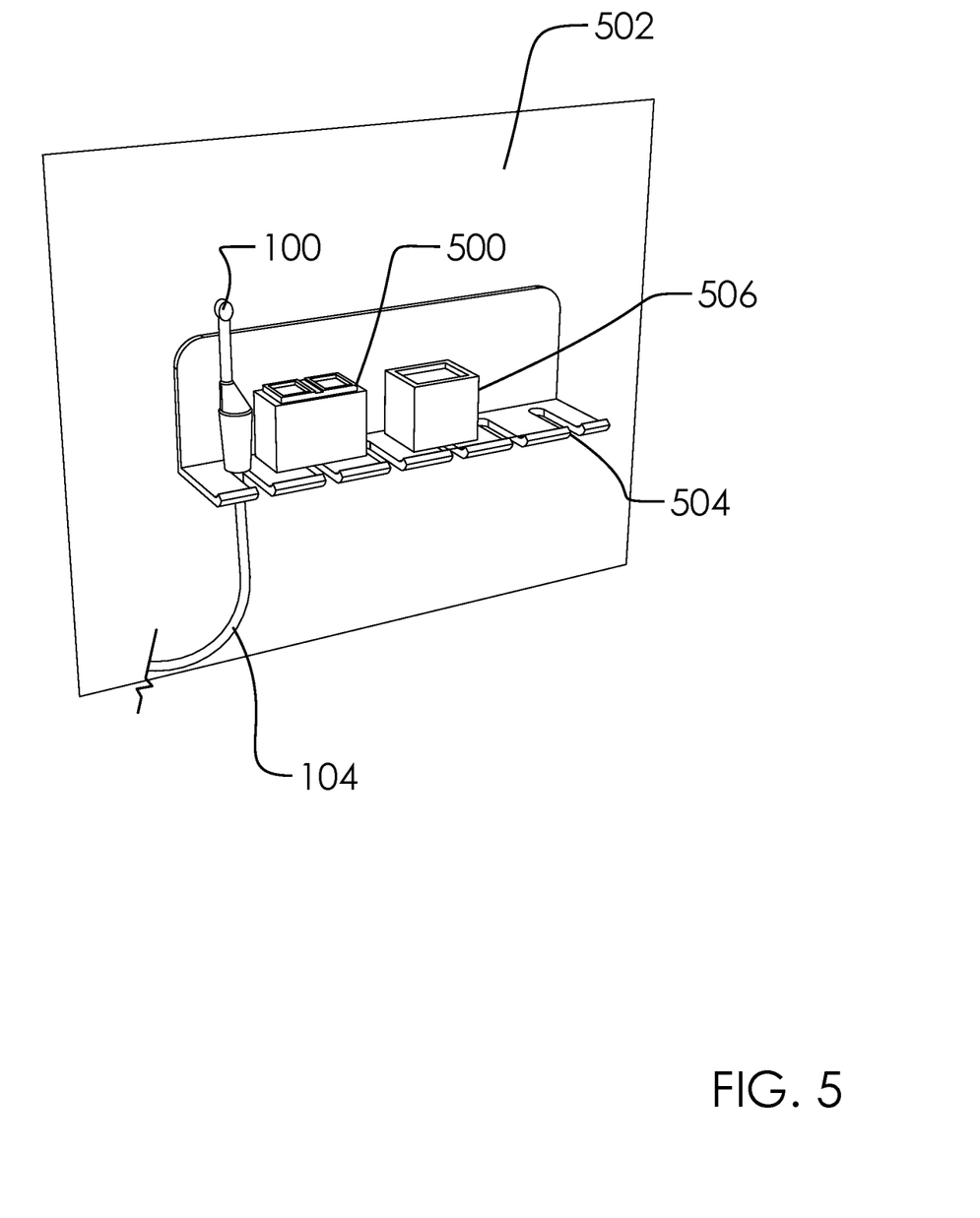
FIG. 5 illustrates a perspective overview of said probe 100 on a rack 504 hanging on a wall 502.

FIG. 5 illustrates a perspective overview of said probe 100 on a rack 504 hanging on a wall 502.

In one embodiment, said probe 100 can be stored as illustrated. Further, said rack 504 can comprise a control box 500 which can comprise a cleaning system.

In one embodiment, said probe sleeve 200 can be dispensed from a dispenser 506, which can be located proximate to said control box 500. In one embodiment, said dispenser 506 can comprise a box being design similar to a tissue box with a top aperture for access to a plurality of said probe sleeve 200.

Figure 6:
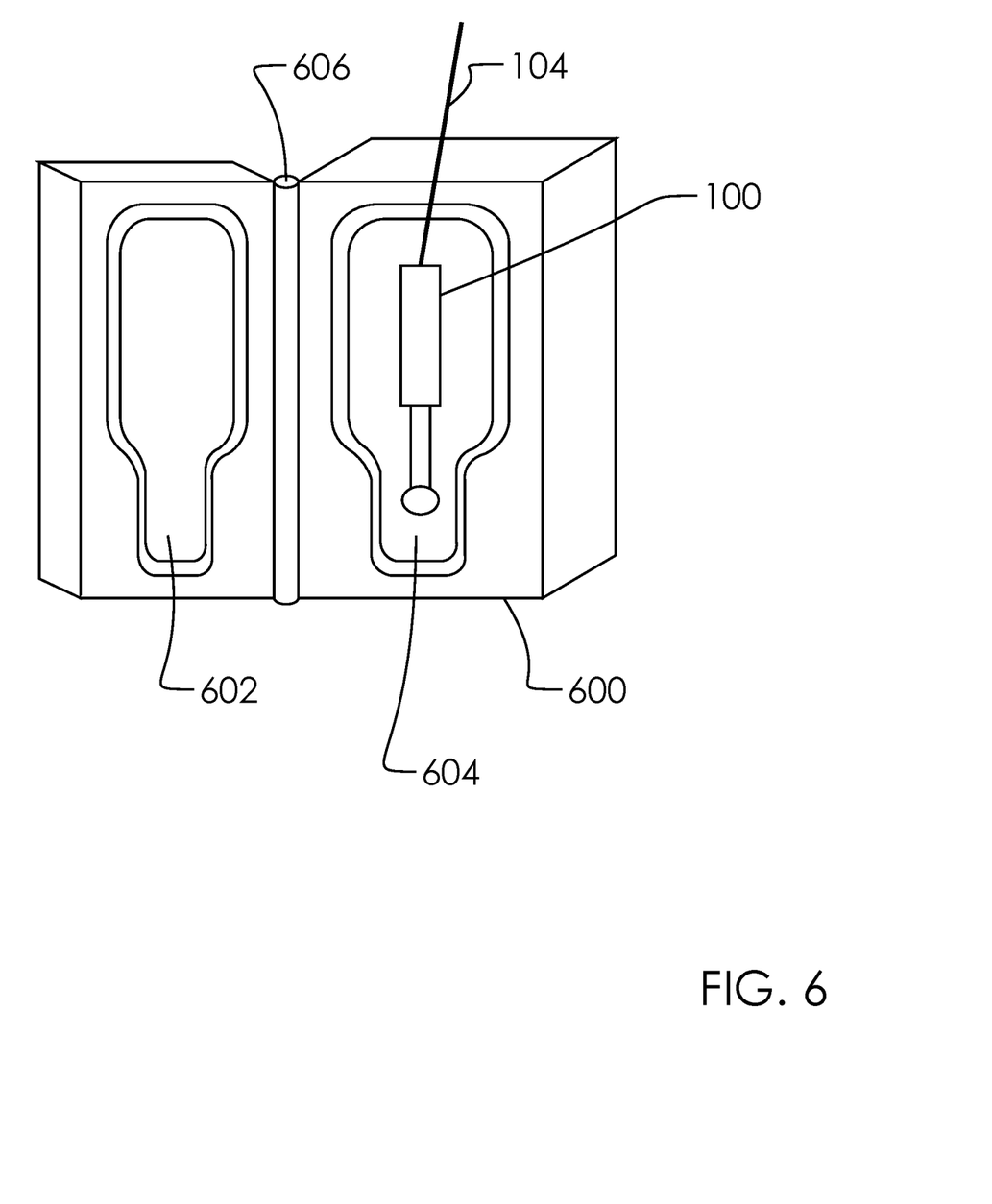
FIG. 6 illustrates a perspective overview of a sanitizing system 600, as is known in the art.

FIG. 6 illustrates a perspective overview of a sanitizing system 600, as is known in the art.

In one embodiment, said sanitizing system 600 can comprise a first cavity 602, a second cavity 604, and a hinge 606. In one embodiment, said probe 100 can be sanitized in said sanitizing system 600. Said sanitizing system 600, as is known in the art, can close around said probe 100 and a portion of said probe cord 104, inject chemicals and/or heat into said first cavity 602 and said second cavity 604, and thereby sanitize said probe 100.

Using said sanitizing system 600 can comprise inserting a chemical indicator from said sanitizing system 600, removing said probe 100, wiping down said probe 100, discarding gloves, and documenting the cleaning.

In another embodiment, said probe 100 can be cleaned with hazardous chemicals requiring approximately fifteen minute soak periods followed by water soaking periods.

Figure 7A:
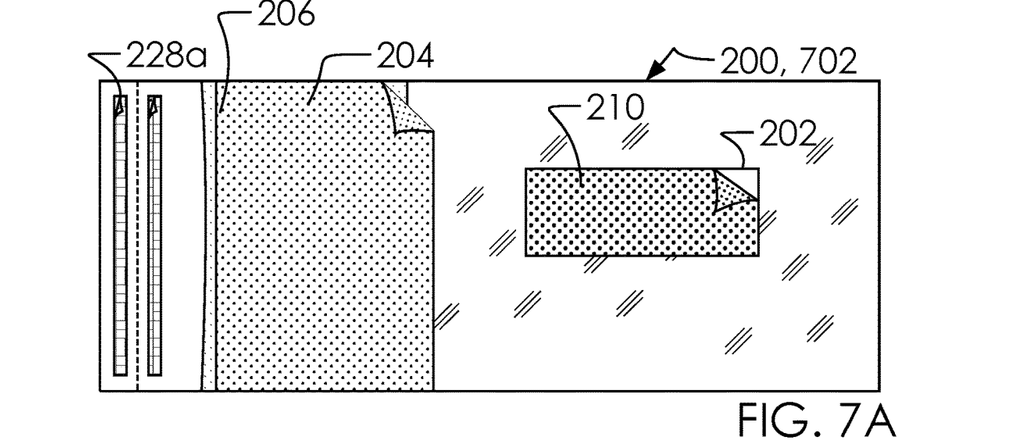
FIGS. 7A, 7B and 7C illustrate said probe sleeve 200 holding said probe 100, illustrated in a first configuration 702, a second configuration 704, and a third configuration 706, respectively.
Figure 7B:
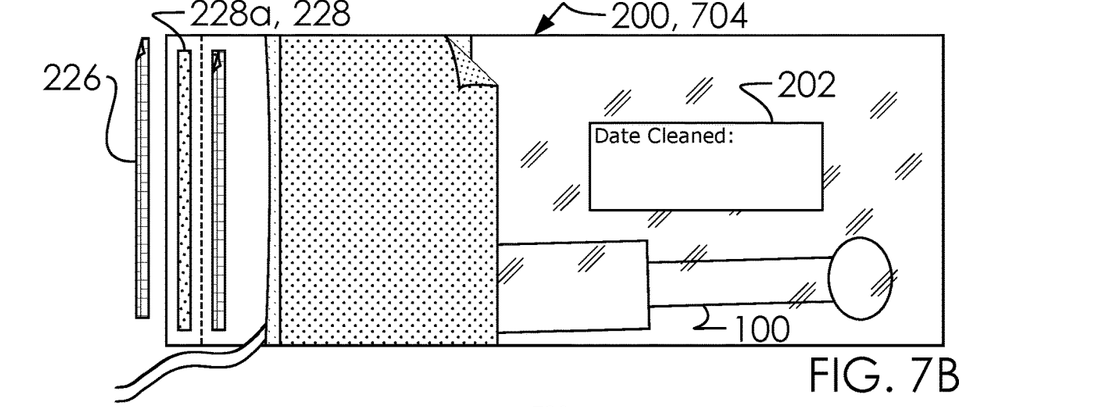
Figure 7C:
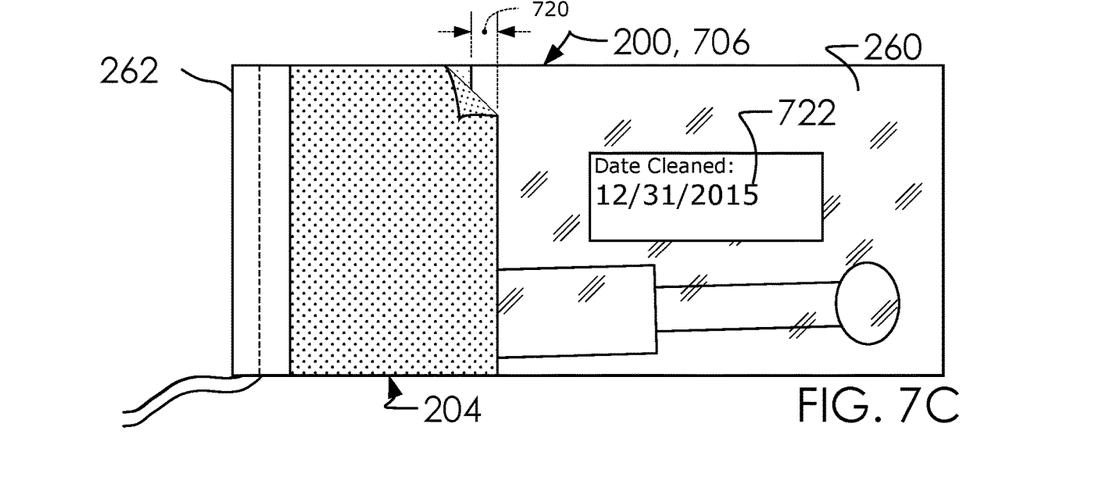

FIGS. 7A, 7B and 7C illustrate said probe sleeve 200 holding said probe 100, illustrated in a first configuration 702, a second configuration 704, and a third configuration 706, respectively.

Said first configuration 702 can comprise said probe sleeve 200 ready to receive said probe 100. Said second configuration 704 can comprise said probe sleeve 200 inserted into said probe sleeve 200 and with said label cover 210 removed ready to make the date of cleaning. Said third configuration 706 can comprise said probe sleeve 200 containing said probe 100 being clean, sealed and ready for use.

In one embodiment, closing said flap portion 262 can comprise removing one among said one or more adhesive strips 228 (such as said first strip 228a), folding said flap portion 262 over said mouth 224 and fixing said flap portion 262 onto said first indicator zone 204. In one embodiment, an advantage of affixing one among said one or more adhesive strips 228 to said first indicator zone 204 is that by opening said probe sleeve 200 again, said first indicator zone 204 will be removed while opening said probe sleeve 200. Accordingly, where said first indicator zone 204 is green and said second indicator zone 206 is red, a user of said probe sleeve 200 will immediately know if said probe 100 is clean by the color on said probe sleeve 200.

In one embodiment, a user of said probe 100 can indicate its sanitization status by removing portions of said probe sleeve 200 at the time of an event.

In one embodiment, said first indicator zone 204 can comprise a pulling flap 720. In one embodiment, said pulling flap 720 can comprise a portion of said first indicator zone 204 which overlaps past said second indicator zone 206 to enable a user of said probe sleeve 200 to pull said first indicator zone 204 away from said second indicator zone 206. In one embodiment, removing said second indicator zone 206 from said first indicator zone 204 can comprise taking a portion of said flap portion 262 along with it, as described below.

In one embodiment, said label 202 can receive a date marking 722.

Figure 8A:
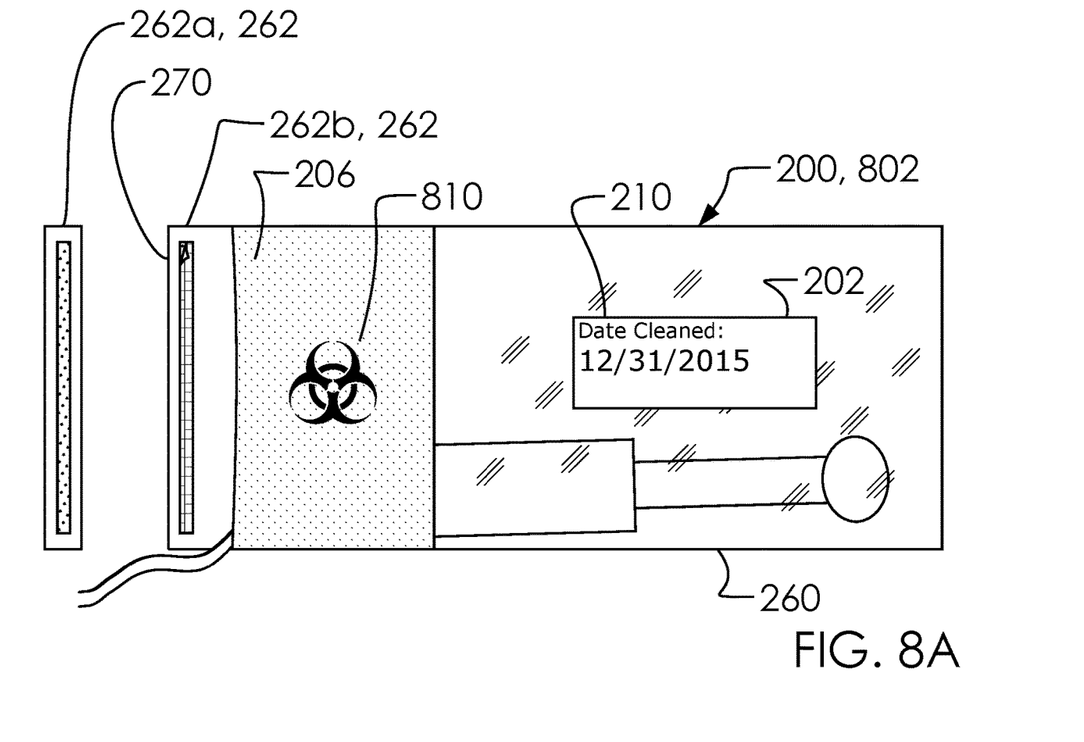
FIGS. 8A and 8B illustrate said probe sleeve 200 with said first indicator zone 204 exposed, illustrated in a fourth configuration 802 and a fifth configuration 804, respectively.
Figure 8B:
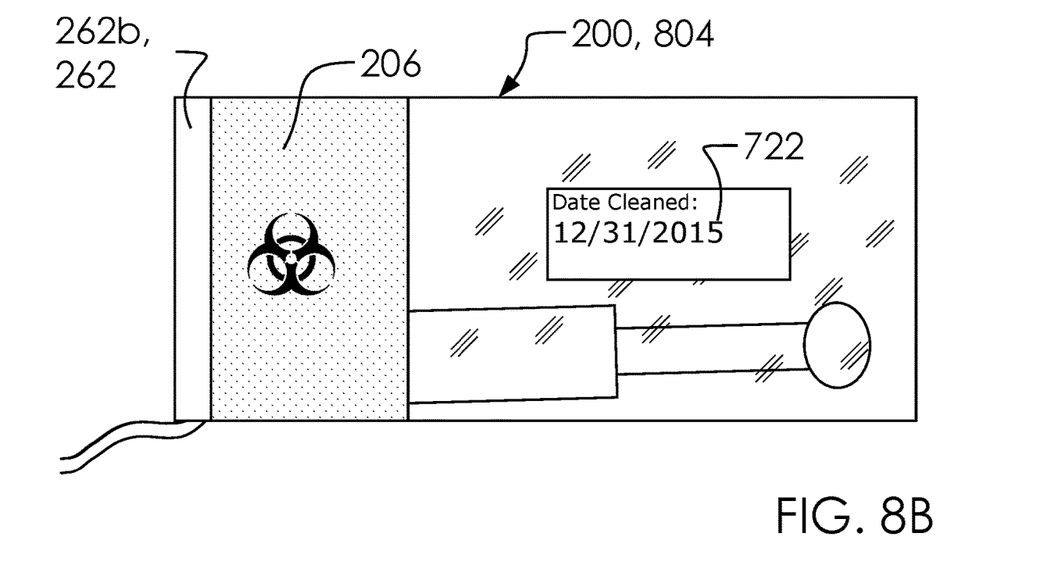

FIGS. 8A and 8B illustrate said probe sleeve 200 with said first indicator zone 204 exposed, illustrated in a fourth configuration 802 and a fifth configuration 804, respectively.

In one embodiment, said flap portion 262 can comprise a first flap portion 262a and a second flap portion 262b. In one embodiment, removing said first indicator zone 204 can expose a portion of said second indicator zone 206, as illustrated. In one embodiment, said second indicator zone 206 can comprise a biohazard symbol 810. In one embodiment, removing said probe 100 from, said probe sleeve 200 can comprise cause said first indicator zone 204 to be ripped off. In one embodiment, said first indicator zone 204 can remain attached to said first strip 228a which is attached to said first flap portion 262a. In one embodiment, removing said first indicator zone 204 can cause said first flap portion 262a to rip apart from said second flap portion 262b substantially along said perforation 270.

In one embodiment, said second indicator zone 206 can mean that once said probe 100 has been reinserted into said probe sleeve 200 it is no longer fit for human use. Most likely because said probe 100 has been used in a medical procedure already. This secondary use of said probe sleeve 200 after a procedure may be skipped if the probe is cleaned after such a procedure. Accordingly, said probe 100 may be cleaned and put into a new sleeve. Otherwise, said probe sleeve 200 with said biohazard symbol 810 showing can be used to store unclean instruments awaiting a cleaning.

Figure 9A:
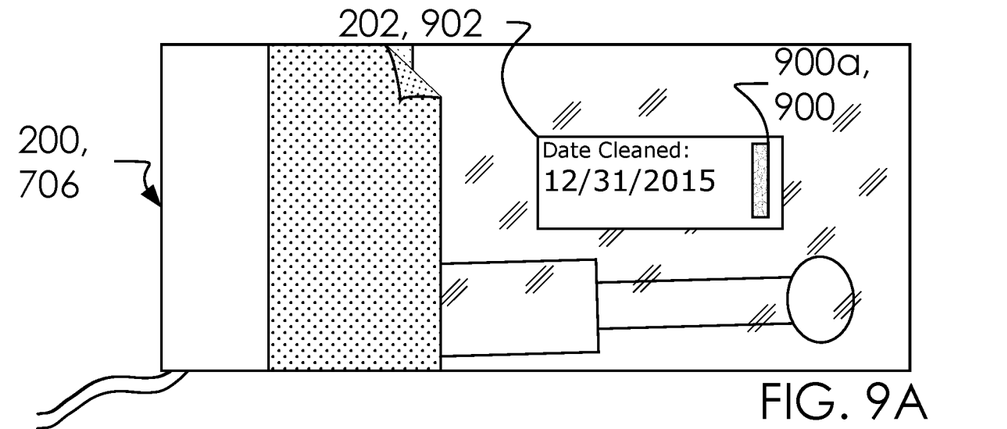
FIGS. 9A, 9B and 9C illustrate said label 202 in a first stage 902, second stage 904 and a third stage 906.
Figure 9B:
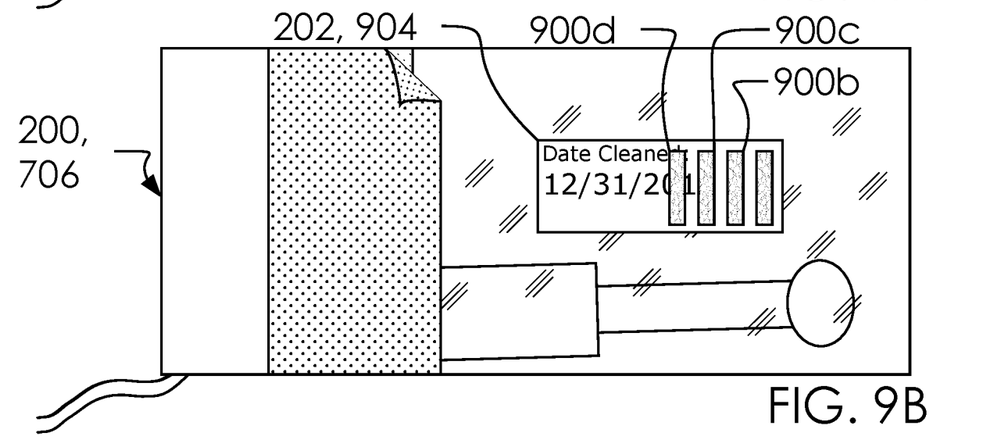
Figure 9C:
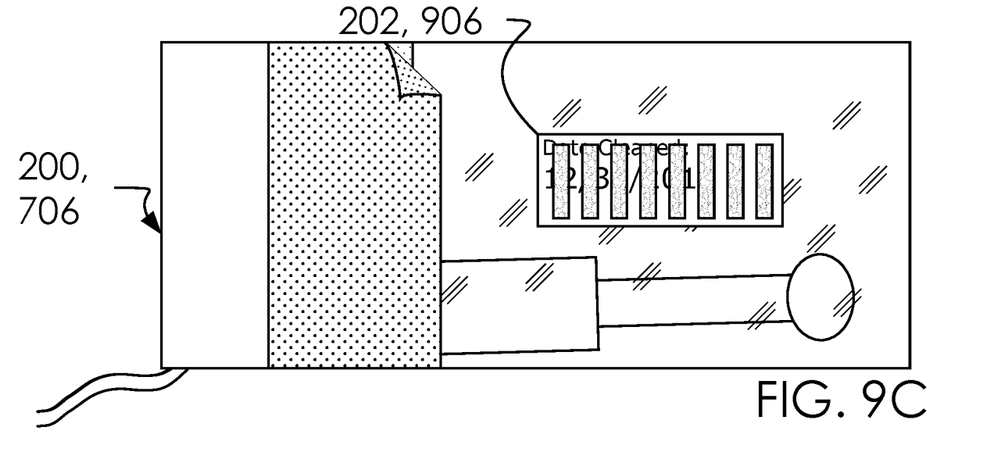

FIGS. 9A, 9B and 9C illustrate said label 202 in a first stage 902, second stage 904 and a third stage 906.

In one embodiment, said label 202 can comprise a one or more gradually appearing markers 900. In one embodiment, said one or more gradually appearing markers 900 can comprise a first marker 900a, a second marker 900b, a third marker 900c and a fourth marker 900d.

In one embodiment, said one or more gradually appearing markers 900 can appear in stages beginning with the removal of said label cover 210 from said probe sleeve 200. For example, when said label cover 210 is removed from said probe sleeve 200, none of said one or more gradually appearing markers 900 are visible. Subsequently, more and more among said one or more gradually appearing markers 900 can appear to indicate the time since said label cover 210 has been removed. Accordingly, a user of said probe sleeve 200 will know how long ago said probe 100 has been cleaned. Suitable appearing inks are known in the art and need not be disclosed here.

Figure 10A:
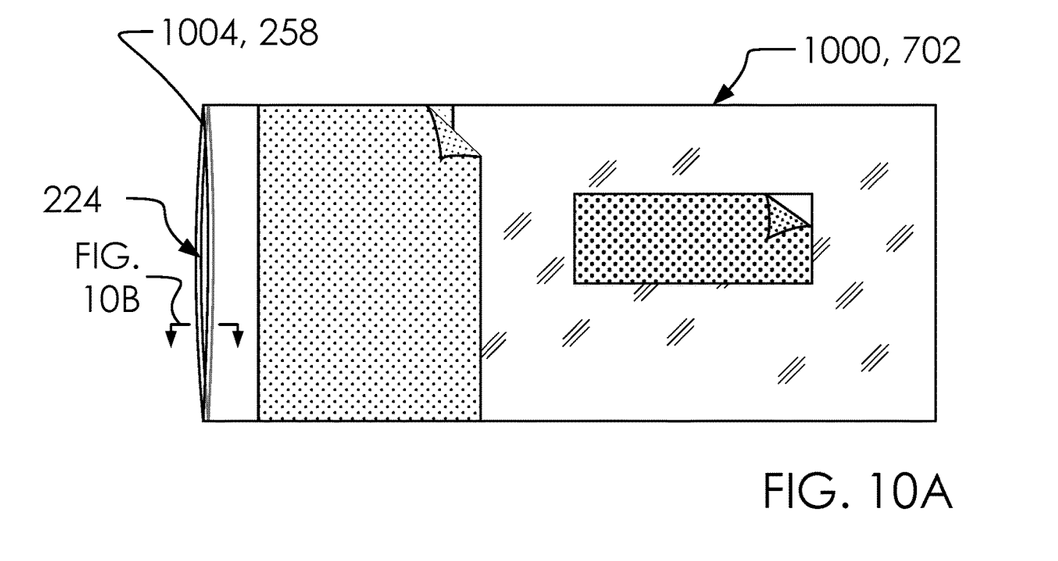
FIGS. 10A and 10B illustrate a probe sleeve 1000 with a resealing mouth 1004 in said first configuration 702, and a detailed cross-section view of said resealing mouth 1004.
Figure 10B:
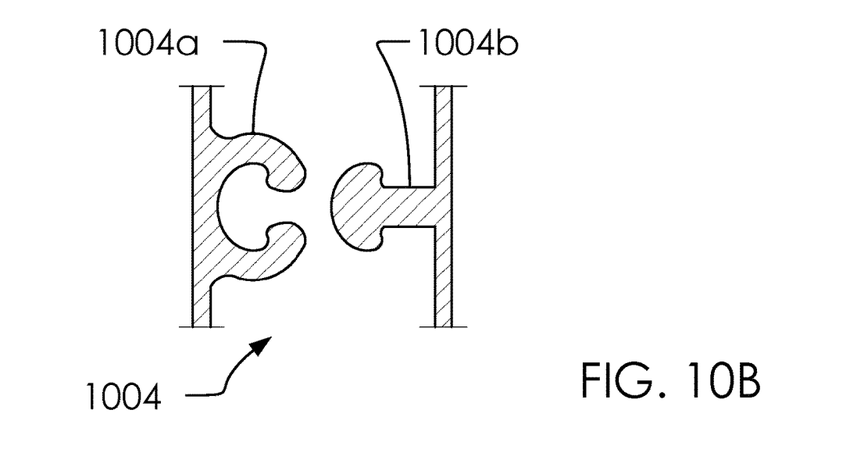

FIGS. 10A and 10B illustrate a probe sleeve 1000 with a resealing mouth 1004 in said first configuration 702, and a detailed cross-section view of said resealing mouth 1004.

In one embodiment, said probe sleeve 1000 can comprise said sealing system 258 which can comprise said resealing mouth 1004. In one embodiment, said sealing system 258 (said resealing mouth 1004) can selectively close over a portion of said mouth 224.

In one embodiment, said resealing mouth 1004 can comprise a first portion 1004a and a second portion 1004b, as is known in the art. One example of said resealing mouth 1004 can be found in the common kitchen resealing food bag. Accordingly, said probe sleeve 1000 can be used without the complexity of said one or more adhesive strips 228 and nonetheless provide the protection of said probe 100, as described and illustrated elsewhere herein.

Figure 11A:
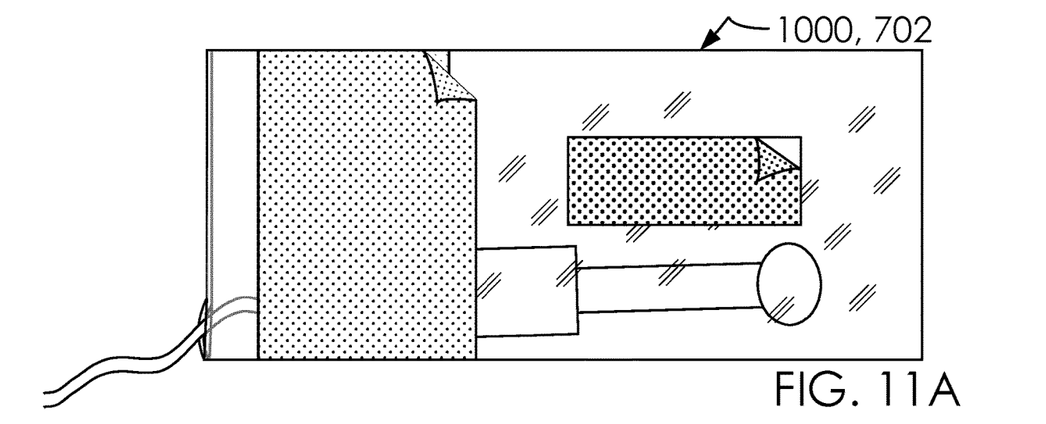
FIGS. 11A, 11B and 11C illustrate said probe sleeve 1000 in said first configuration 702, said third configuration 706, and said fifth configuration 804, respectively.
Figure 11B:
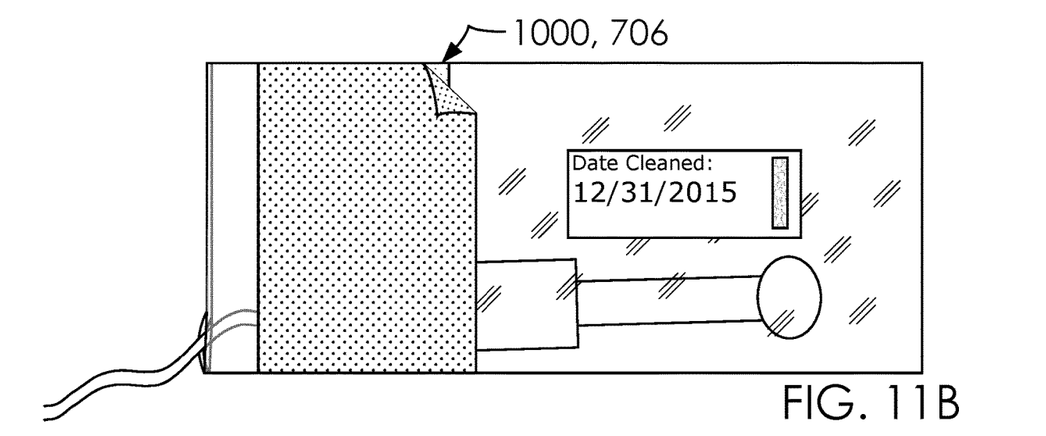
Figure 11C:
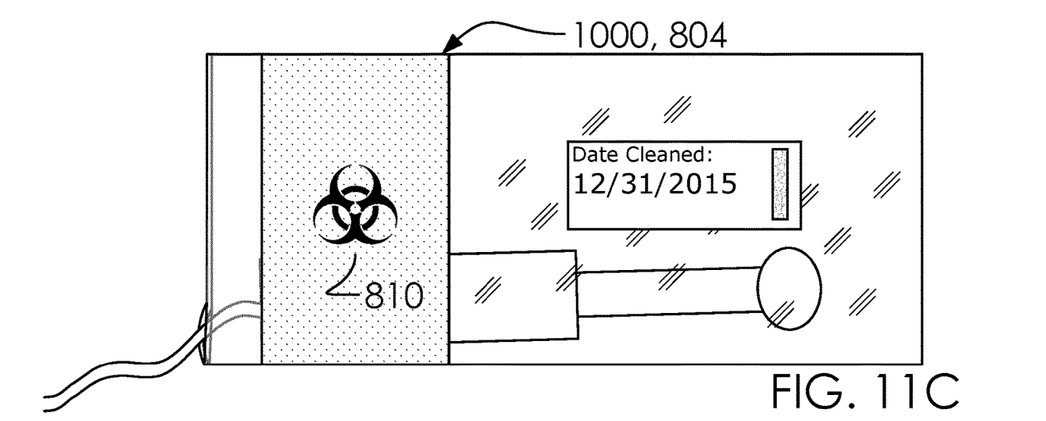

FIGS. 11A, 11B and 11C illustrate said probe sleeve 1000 in said first configuration 702, said third configuration 706, and said fifth configuration 804, respectively.

Said probe sleeve 1000 can progress through the same stages as said probe sleeve 200, such as said first configuration 702 with a recently cleaned probe 100 therein, said third configuration 706 with said label 202 having been filled out, and said fifth configuration 804 with said probe 100 having been used and said biohazard symbol 810 exposed. Accordingly, said fifth configuration 804 can represent a convenience for the current system, but it is optional.

Various changes in the details of the illustrated operational methods are possible without departing from the scope of the following claims. Some embodiments may combine the activities described herein as being separate steps. Similarly, one or more of the described steps may be omitted, depending upon the specific operational environment the method is being implemented in. It is to be understood that the above description is intended to be illustrative, and not restrictive. For example, the above-described embodiments may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein."

The invention claimed is:

1. A probe sleeve for holding a probe in various stages of cleanliness with indicators thereto, comprising:
   an envelope portion, a sealing system, and a plurality of indicator zones;
   said envelope portion comprising a mouth;
   said mouth is operative to receive and release the probe;
   said envelope portion is operative to hold the probe;
   said plurality of indicator zones comprise a first indicator zone and a second indicator zone;
   said plurality of indicator zones each displays a status indicator related to the state of the probe;
   said sealing system is configured to selectively close and open said mouth;
   said first indicator zone is operable to signify that the probe is clean;
   said second indicator zone is operable to signify that the probe is not clean;
   said probe sleeve further comprises a label;
   said label comprises a one or more gradually appearing markers;
   said one or more gradually appearing markers activate when said label cover is removed from said label; and
   said one or more gradually appearing markers are operable to signify a time since said label cover has been removed from said label.

2. The probe sleeve of claim 1, wherein:
   said probe sleeve further comprises a label cover; and
   said label cover selectively covers a portion of said label.

3. The probe sleeve of claim 1, wherein:
   said sealing system comprises a flap portion;
   said flap portion comprises one or more adhesive strips; and
   said one or more adhesive strips are operable to selectively close a portion of said flap portion over said resealing mouth.

4. The probe sleeve of claim 3, wherein:
   said one or more adhesive strips comprise a first strip and a second strip;
   said flap portion comprises a first flap portion and a second flap portion;
   said first flap portion comprises said first strip; and
   said second flap portion comprises said second strip.

5. The probe sleeve of claim 4, wherein:
   said flap portion comprises a perforation between said first flap portion and said second flap portion.

6. The probe sleeve of claim 5, wherein:
   said first indicator zone is arranged on top of said second indicator zone;
   said first indicator zone comprises a first side and a second side;
   said second side comprises an adhesive;
   removing said first indicator zone from said second indicator zone exposes a portion of said second indicator zone;
   said first flap portion with said first strip are configured to attach to a portion of said first indicator zone; and
   said first indicator zone is configured to remove said first flap portion with said first strip when opening said probe sleeve to remove the probe.

7. The probe sleeve of claim 1, wherein:
   said first indicator zone is arranged on top of said second indicator zone;
   said first indicator zone comprises a first side and a second side;
   said second side comprises an adhesive; and
   removing said first indicator zone from said second indicator zone exposes a portion of said second indicator zone.

8. The probe sleeve of claim 7, wherein:
   said second indicator zone comprises a biohazard symbol.

9. A probe sleeve for holding a probe in various stages of cleanliness with indicators thereto, comprising:
   an envelope portion, a flap portion, and a plurality of indicator labels;
   said envelope portion comprising a mouth;
   said mouth is operative to receive and release the probe;
   said envelope portion is operative to hold the probe;
   said plurality of indicator labels comprise a first indicator label and a second indicator label;
   said plurality of indicator labels each displays a status indicator related to the state of the probe;
   said flap portion comprises one or more adhesive strips; and
   said one or more adhesive strips are operable to selectively close a portion of said flap portion over said mouth;
   said flap portion is configured to selectively close and open said mouth;
   said first indicator label is operable to signify that the probe is clean;
   said second indicator label is operable to signify that the probe is not clean;
   said probe sleeve further comprises a label;
   said probe sleeve further comprises a label cover;
   said label cover selectively covers a portion of said label;
   said label comprises one or more gradually appearing markers;
   said one or more gradually appearing markers activate when said label cover is removed from said label; and
   said one or more gradually appearing markers are operable to signify a time since said label cover has been removed from said label.

10. A probe sleeve for holding a probe in various stages of cleanliness with indicators thereto, comprising:
    an envelope portion, a flap portion, and a plurality of indicator zones;
    said envelope portion comprising a mouth;
    said mouth is operative to receive and release the probe;
    said envelope portion is operative to hold the probe;
    said plurality of indicator zones comprise a first indicator zone and a second indicator zone;

said plurality of indicator zones each displays a status indicator related to the state of the probe;
said flap portion comprises one or more adhesive strips;
said one or more adhesive strips are operable to selectively close a portion of said flap portion over said mouth;
said flap portion is configured to selectively close and open said mouth;
said first indicator zone is operable to signify that the probe is clean;
said second indicator zone is operable to signify that the probe is not clean;
said one or more adhesive strips comprise a first strip and a second strip;
said flap portion comprises a first flap portion and a second flap portion;
said first flap portion comprises said first strip;
said second flap portion comprises said second strip;
said flap portion comprises a perforation between said first flap portion and said second flap portion;
said first indicator zone is arranged on top of said second indicator zone;
said first indicator zone comprises a first side and a second side;
said second side comprises an adhesive;
removing said first indicator zone from said second indicator zone exposes a portion of said second indicator zone;
said first flap portion with said first strip are configured to attach to a portion of said first indicator zone; and
said first indicator zone is configured to remove said first flap portion with said first indicator zone when opening said probe sleeve to remove the probe.

11. A probe sleeve for holding a probe in various stages of cleanliness with indicators thereto, comprising:
an envelope portion, and a sealing system;
said envelope portion comprising a mouth;
said mouth is operative to receive and release the probe;
said envelope portion is operative to hold the probe;
said plurality of indicator zones display a status indicator related to the state of the probe;
said sealing system is configured to selectively close and open said mouth;
said probe sleeve further comprises a label;
said label comprises a one or more gradually appearing markers;
said one or more gradually appearing markers activate when said label cover is removed from said label; and
said one or more gradually appearing markers are operable to signify a time since said label cover has been removed from said label.

* * * * *